United States Patent [19]

Adachi et al.

[11] Patent Number: 5,527,954
[45] Date of Patent: Jun. 18, 1996

[54] PROCESS FOR THE PRODUCTION OF 2-FLUOROISOBUTYRIC ACID OR ITS ESTER

[75] Inventors: Ryoichi Adachi; Masahiro Nishii, both of Sodegaura; Tadashi Kikukawa; Yasuhito Kotsuji, both of Amagasaki, all of Japan

[73] Assignee: Idemitsu Kosan Co., Ltd., Tokyo, Japan

[21] Appl. No.: 343,551

[22] PCT Filed: Apr. 7, 1994

[86] PCT No.: PCT/JP94/00588

§ 371 Date: Jan. 26, 1995

§ 102(e) Date: Jan. 26, 1995

[87] PCT Pub. No.: WO92/24086

PCT Pub. Date: Oct. 27, 1994

[30] Foreign Application Priority Data

Apr. 8, 1993 [JP] Japan ................................ 5-082137

[51] Int. Cl.$^6$ ............................................. C07C 69/63
[52] U.S. Cl. ......................... 560/227; 562/602; 562/603; 562/605
[58] Field of Search ........................... 560/227; 562/602, 562/603, 605

[56] References Cited

FOREIGN PATENT DOCUMENTS

| 0506059 | 9/1992 | European Pat. Off. . |
|---|---|---|
| 405043515 | 2/1993 | Japan . |
| 405085987 | 4/1993 | Japan . |
| 405301844 | 11/1993 | Japan . |

*Primary Examiner*—Gary Geist
*Assistant Examiner*—Rosalynd A. Williams
*Attorney, Agent, or Firm*—Frishauf, Holtz, Goodman, Langer & Chick

[57] ABSTRACT

Provided is a process for the production of 2-fluoroisobutyric acid or its ester, which comprises reacting 2-hydroxyisobutyric acid or its ester with thionyl chloride and a hydrogen fluoride source.

9 Claims, No Drawings

PROCESS FOR THE PRODUCTION OF 2-FLUOROISOBUTYRIC ACID OR ITS ESTER

This application is a 371 of PCT/JP94/00588, filed April 07, 1994

FILED OF INDUSTRIAL UTILIZATION

The present invention relates to a process for the production of 2-fluoroisobutyric acid or an ester thereof. The 2-fluoroisobutyric acid or the ester thereof, obtained by the present invention, is useful as an intermediate for a triazine-based herbicide.

PRIOR ART

As a triazine-based herbicide, International PCT Publication WO90/09378 discloses a triazine-based herbicide in which a phenoxyalkylamino group is substituted on a triazine ring, for example, as shown by the formula,

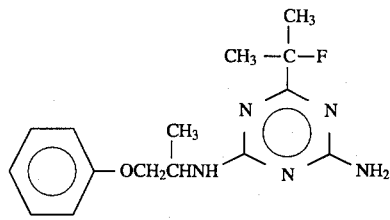

and this Publication describes that the above triazine-based herbicide has remarkable advantages in that it is not only excellent in herbicidal activity but also free from phytotoxicity to rice on a paddy field.

The phenoxyalkylamino-substituted triazine-based herbicide of this type is obtained by reacting 2-fluoroisobutyrate with 2-phenoxy-1-methyl-ethylbiguanide. As a method for producing 2-fluoroisobutyrate used in the above reaction, U.S. Pat. No. 5,175,345 discloses a method in which 2-hydroxyisobutyrate is reacted (a) with fluorosulfuric acid in the presence or absence of a hydrogen fluoride source or (b) with chlorosulfuric acid in the presence of hydrogen fluoride. This conventional method is shown by a reaction scheme below.

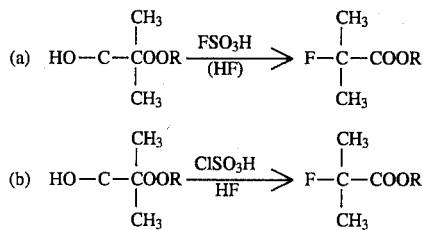

PROBLEMS TO BE SOLVED BY THE INVENTION

In the method using 2-hydroxyisobutyrate as a raw material, described in the above U.S. Patent, 2-fluoroisobutyrate can be obtained at relatively high yields, while a large amount of methacrylate having a boiling point close to that of the 2-fluoroisobutyrate is formed as a byproduct. Industrially disadvantageously, therefore, the post treatment for removing the methacrylate formed as a byproduct is complicated. For achieving high yields, further, a large amount (at least 6 mol per mole of the raw material) of fluorosulfuric acid is required, and it is required to neutralize unreacted fluorosulfuric acid with an alkali such as $Ca(OH)_2$ before disposal. There is hence another defect in that a large amount of waste is formed.

It is therefore an object of the present invention to provide a process which enables the production of 2-fluoroisobutyric acid or its ester in a simple apparatus at high yields while preventing the formation of a byproduct which is difficult to separate.

MEANS TO SOLVE THE PROBLEMS

The present inventors have found that, by reacting 2-hydroxyisobutyric acid or its ester with thionyl chloride and a hydrogen fluoride source, 2-fluoroisobutyric acid or its ester can be produced in a simple apparatus at high yields while preventing the formation of a byproduct, and on basis of this finding, the present invention has been completed.

The object of the present invention therefore consists in a process for the production of 2-fluoroisobutyric acid or its ester, which comprises reacting 2-hydroxyisobutyric acid or its ester with thionyl chloride and a hydrogen fluoride source.

The present invention will be detailed hereinafter.

In the process for the production of 2-fluoroisobutyric acid or its ester, provided by the present invention, the 2-ydroxyisobutyric acid or its ester used as a starting material includes, for example, compounds of the general formula (I),

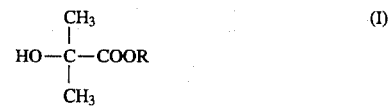

(wherein R is a hydrogen atom or a lower alkyl group).

The compound of the general formula (I) in which R is a hydrogen atom is 2-hydroxyisobutyric acid, and the compound of the general formula (I) in which R is a lower alkyl group is 2-hydroxyisobutyrate. The alkyl group for R includes alkyl groups having to 1 to 4 carbon atoms such as methyl, ethyl, n-propyl, i-propyl, n-butyl, i-butyl, sec-butyl and t-butyl groups.

According to the present invention, the above 2-ydroxyisobutyric acid or its ester is reacted with thionyl chloride and a hydrogen fluoride source, whereby 2-fluoroisobutyric acid or its ester is obtained.

The raw material for the reaction in the present invention is 2-hydroxyisobutyric acid or its ester, while 2-hydroxyisobutyric acid ester is preferred. The reason therefor is that the ester can give a fluorinated product at higher yields.

When 2-hydroxyisobutyric acid or its ester is allowed to react with thionyl chloride and a hydrogen fluoride source, it is preferred to react the 2-hydroxyisobutyric acid or its ester with thionyl chloride first and then with a hydrogen fluoride source.

The method for reacting 2-hydroxyisobutyric acid or its ester with thionyl chloride and then with a hydrogen fluoride source will be explained.

The reaction of 2-hydroxyisobutyric acid or its ester wi.. thionyl chloride in a first step is carried out by adding thionyl chloride to 2-hydroxyisobutyric acid or its ester and stirring the mixture, or by adding 2-hydroxyisobutyric acid or its ester to thionyl chloride and stirring the mixture. In this reaction, it is preferred to use thionyl chloride in an amount of 0.5 to 5 mol per mole of the 2-hydroxyisobutyric acid or its ester, and particularly preferably, the molar amount of thionyl chloride is 0.8 to 1.5 times as large as the molar amount of the 2-hydroxyisobutyric acid or its ester.

The reaction temperature is preferably −30 to 50° C., particularly preferably −20 to 20° C. The reaction time is preferably 0.5 to 10 hours, particularly preferably 1 to 5 hours.

In the above reaction in the first step, a solvent is not essential, while an organic solvent inert to the above reactants may be used. The organic solvent includes a saturated aliphatic or aromatic hydrocarbon, a saturated aliphatic or aromatic halogenated hydrocarbon, and a saturated aliphatic or aromatic ester.

The reaction with a fluoride source in a second step is carried out by mixing chlorosulfite (corresponding to an intermediate for the intended compound, 2-fluoroisobutyric acid or its ester) as a reaction product in the reaction mixture obtained in the first step with a hydrogen fluoride source without or after isolating the chlorosulfite. The mixing of these two is carried out by adding the above reaction mixture or the isolated reaction product to a hydrogen fluoride Source, or, reversely, by adding a hydrogen fluoride source to the above reaction mixture or the isolated reaction product.

The hydrogen fluoride source is selected from anhydrous hydrogen fluoride and a mixture of hydrogen fluoride with an amine. The hydrogen fluoride/amine amount ratio in the above mixture is preferably 50/50 to 99/1 (w/w). The above amine includes aromatic amines such as pyridine, melamine and collidine and tertiary aliphatic amines such as trimethylamine, triethylamine and tributylamine. The above hydrogen fluoride source is only required to be in the state of hydrogen fluoride at the time of the reaction, and therefore, a hydrogen fluoride precursor may be charged to the reaction system to generate hydrogen fluoride in the reaction system.

In the above reaction in the second step, the amount of the hydrogen fluoride per mole of 2-hydroxyisobutyric acid or its ester is preferably 1 to 50 mol, more preferably 5 to 30 mol, particularly preferably 7 to 15 mol. The amount of the hydrogen fluoride is most preferably 10 mol, or about 10 mol, per mole of 2-hydroxyisobutyric acid or its ester.

The temperature when the mixture with hydrogen fluoride is formed is preferably −78 to 10° C., particularly preferably −78 to 0° C., most preferably −78° C. to −10° C.

The reaction temperature after the mixture with hydrogen fluoride is formed is preferably −30 to 100° C., particularly preferably −20 to 50° C., and the reaction time is preferably 0.5 to 30 hours, particularly preferably 1 to 20 hours.

In the above reaction in the second step, a solvent is not essential, either, while there may be used an inert solvent such as a saturated aliphatic or aromatic hydrocarbon, a saturated aliphatic or aromatic halogenated hydrocarbon, or a saturated aliphatic or aromatic ester. It is preferred to use solvents of the same kind as a solvent for the reaction in the first step and the reaction in the second step.

After the reaction in the second step is completed, the intended compound, 2-fluoroisobutyric acid or its ester, is isolated from the reaction mixture by a known method. When solvent extraction is used as a method for the isolation, methylene chloride is a preferred solvent.

The reactions in the first and second step may be carried out under atmospheric pressure or under elevated pressure.

The foregoing description has explained a method in which thionyl chloride is reacted first and then the hydrogen fluoride source is added. However, thionyl chloride and the hydrogen fluoride source may be simultaneously added and reacted.

According to the process of the present invention, 2-hydroxyisobutyric acid or its ester is used as a raw material, and 2-fluoroisobutyric acid or its ester can be produced in a simple apparatus at high yields while preventing the formation of a byproduct. Therefore, the present invention has industrially great significance.

EXAMPLES

The present invention will be further explained hereinafter with reference to Examples. However, the present invention shall not be limited to these Examples.

Example 1

A reactor made of glass was charged with 10.70 g (90.7 mmol) of methyl 2-hydroxyisobutyrate, and 11.47 g (96.4 mmol) of thionyl chloride was dropwise added with ice cooling. After the dropwise addition was completed, the mixture was stirred for 3 hours with ice cooling, during which the reaction mixture had a temperature of 0 to 10° C. A reactor made of stainless steel was flushed with argon, and then charged with 18.7 g (935 mmol) of anhydrous hydrogen fluoride, and the above reaction mixture was dropwise added at −10° C. After the addition, the reactor was sealed, and the mixture was stirred at 20° C. for 18 hours.

The resultant reaction mixture was poured onto ice, and extracted with methylene chloride. An organic layer was washed with water, a sodium hydrogencarbonate aqueous solution and a saturated sodium chloride aqueous solution in this order, and then dried over anhydrous sodium sulfate. Methylene chloride was distilled off under reduced pressure, and then the remainder was distilled to give 7.90 g (yield 73% of methyl 2-fluoroisobutyrate having a boiling point of 70° C. (150 mmHg). The amount of methyl methacrylate formed as a byproduct was 0.7%.

Example 2

The reactions in Example 1 were repeated in the same manner as in Example 1 except that the amount of methyl 2-hydroxyisobutyrate was changed to 10.29 g (87.1 mmol) and that the amount of anhydrous hydrogen fluoride was changed to 9.1 g (455 mmol). As a result, 7.22 g (yield 69%) of methyl 2-fluoroisobutyrate was obtained. The amount of methyl methacrylate formed as a byproduct was 3.9%.

Example 3

A reactor made of glass was charged with 11.40 g (95.8 mmol) of thionyl chloride, and 10.25 g (86.9 mmol) of methyl 2-hydroxyisobutyrate was dropwise added with ice cooling. After the dropwise addition was completed, the mixture was stirred for 3 hours with ice cooling, during which the reaction mixture had a temperature of 0 to 10° C. A reactor made of stainless steel was flushed with argon, and then charged with 17.5 g (875 mmol) of anhydrous hydrogen fluoride, and the above reaction mixture was dropwise added at −10° C. After the addition, the reactor was sealed, and the mixture was stirred at 20° C. for 18 hours.

The resultant reaction mixture was poured onto ice, and extracted with methylene chloride. An organic layer was washed with water, a sodium hydrogencarbonate aqueous solution and a saturated sodium chloride aqueous solution in this order, and then dried over anhydrous sodium sulfate. Methylene chloride was distilled off under reduced pressure, and then the remainder was distilled to give 7.80 g (yield 74% of methyl 2-fluoroisobutyrate having a boiling point of 70° C. (150 mmHg). The amount of methyl methacrylate formed as a byproduct was 2.1%.

Examples 4–16

Methyl 2-fluoroisobutyrate was obtained in the same manner as in Example 3 except that the amounts of methyl 2-hydroxyisobutyrate, thionyl chloride and anhydrous hydrogen fluoride were set as shown in the following Table 1, and that the temperature when a reaction mixture of the methyl 2-hydroxyisobutyrate and thionyl chloride was added to the anhydrous hydrogen fluoride and the temperature and time for the reaction with the anhydrous hydrogen fluoride were changed as shown in Table 1. Table 1 shows the yield of the methyl 2-fluoroisobutyrate and the amount of methyl methacrylate formed as a byproduct.

fluoride is −10° C. or lower, the yield of methyl 2-fluoroisobutyrate is 80 to 81%, or hardly varies. However, when this temperature is −40° C. or lower, the amount of methyl methacrylate formed as a byproduct is small.

(iii) On the basis of the results of Examples 6–11 in which the temperature and time for the reaction with anhydrous hydrogen fluoride were changed, when the temperature is 20° C. and when a short reaction time is employed, the yield of the intended product is low to some extent (in Example 6 where the reaction temperature and times are 20° C. and 18 hours, the yield of the intended product is 81%, while in Example 7 where the

TABLE 1

| Example No. | Amount [g (mmol)] | | | | | Temperature at the time of addition to anhydrous hydrogen fluoride | Temperature and time for reaction with anhydrous hydrogen fluoride | Yield of methyl 2-fluoro isobutyrate | Amount of methyl methacrylate as byproduct |
|---|---|---|---|---|---|---|---|---|---|
| | (A) Methyl 2-hydroxy-isobutyrate | (B) Thionyl chloride | (B)/(A) | (C) Anhydrous hydrogen fluoride | (C)/(A) | | | | |
| 1 | 10.70 (90.7) | 11.47 (96.4) | 1.06 | 18.7 (935) | 10.30 | −10° C. | 20° C., 18 hours | 73% | 0.7% |
| 2 | 10.29 (87.1) | 11.47 (96.4) | 1.11 | 9.1 (455) | 5.22 | −10° C. | 20° C., 18 hours | 69% | 3.9% |
| 3 | 10.25 (86.9) | 11.4 (95.8) | 1.10 | 17.5 (875) | 10.06 | −10° C. | 20° C., 18 hours | 74% | 2.1% |
| 4 | 10.25 (86.9) | 13.1 (110) | 1.27 | 16.1 (805) | 9.26 | −10° C. | 20° C., 18 hours | 80% | 3.1% |
| 5 | 10.73 (90.9) | 14.2 (119) | 1.31 | 17.4 (870) | 9.57 | −40° C. | 20° C., 18 hours | 81% | 1.3% |
| 6 | 10.16 (86.1) | 13.1 (110) | 1.28 | 17.4 (870) | 10.10 | −78° C. | 20° C., 18 hours | 81% | 1.3% |
| 7 | 10.38 (88.0) | 15.7 (132) | 1.50 | 19.3 (965) | 10.09 | −78° C. | 20° C., 5 hours | 73% | 1.2% |
| 8 | 5.04 (42.7) | 7.1 (59.7) | 1.40 | 13.9 (695) | 16.27 | −40° C. | 30° C., 2 hours | 77% | 2.1% |
| 9 | 5.02 (42.5) | 7.1 (59.7) | 1.40 | 11.0 (550) | 12.94 | −40° C. | 30° C., 5 hours | 79% | 1.2% |
| 10 | 5.05 (42.8) | 7.3 (61.3) | 1.43 | 10.7 (535) | 12.50 | −40° C. | 40° C., 2 hours | 77% | 3.7% |
| 11 | 9.99 (84.7) | 11.5 (96.6) | 1.14 | 17.8 (890) | 10.51 | −10° C. | 20° C., 18 hours 30° C., 2 hours*) | 79% | 1.3% |
| 12 | 5.01 (42.5) | 7.0 (58.8) | 1.38 | 27.5 (1,375) | 32.35 | −10° C. | 20° C., 18 hours | 78% | 1.5% |
| 13 | 5.04 (42.7) | 7.0 (58.8) | 1.38 | 16.4 (820) | 19.20 | −10° C. | 20° C., 18 hours | 75% | 1.5% |
| 14 | 5.00 (42.4) | 7.0 (58.8) | 1.39 | 9.7 (485) | 11.44 | −10° C. | 20° C., 18 hours | 77% | 1.6% |
| 15 | 10.20 (86.4) | 13.1 (110) | 1.27 | 17.7 (885) | 10.24 | −10° C. | 20° C., 18 hours | 84% | 2.8% |
| 16 | 10.08 (85.4) | 11.7 (98.3) | 1.15 | 5.7 (285) | 3.33 | −10° C. | 20° C., 18 hours | 80% | 7.2% |

(B)/(A) and (C)/(A) refer to molar ratios of thionyl chloride and anhydrous hydrogen fluoride to methyl 2-hydroxy-isobutyrate.
*) Reacted at 20° C. for 18 hours, and further reacted at 30° C. for 2 hours.

Table 1 shows the following.

(i) On basis of the results of Examples 1 to 16 in which the amount of anhydrous hydrogen fluoride based on the methyl 2-hydroxyisobutyrate was varied, when the amount of anhydrous hydrogen fluoride based on methyl 2-hydroxyisobutyrate is small, as small as 3.33 mol and 5.22 mol per mole of the methyl 2-hydroxyisobutyrate in Examples 16 and 2, the amount of methyl methacrylate formed as a byproduct is large, as large as 7.2% and 3.9%. In contrast, when the amount of anhydrous hydrogen fluoride per mole of methyl 2-hydroxyisobutyrate is 10 mol or in the vicinity of 10 mol, for example, in Examples 1, 6 and 11, the yield of the intended product is high, and the amount of methyl methacrylate formed as a byproduct is small, as small as 0.7%, 1.3% and 1.3%. Even if the amount of anhydrous hydrogen fluoride per mole of 2-hydroxyisobutyrate is increased, for example, to 16.27 mol (Example 8) or 19.20 mol (Example 13), the yield of the intended product and the amount of the byproduct hardly change as compared with a case where the above amount per mole of 2-hydroxyisobutyrate is 10 mol or in the vicinity of 10 mol.

(ii) On the basis of the results of Examples 4, 5 and 6 in which the temperature at the time of the addition to anhydrous hydrogen fluoride was set at −10° C., −40° C. and −78° C., respectively, so long as the temperature at the time of the addition to anhydrous hydrogen reaction temperature and time are 20° C. and 5 hours, the yield of the intended product is 73%). However, if it is considered that the short reaction time is employed, this yield is to be satisfactory. When the reaction temperature is increased from 20° C. to 30° C. or 40° C., the amount of methyl methacrylate formed as a byproduct increases (in Example 7 where the reaction temperature and time are 20° C. and 5 hours, the amount of the byproduct is 1.2%, while in Example 8 where the reaction temperature and time are 30° C. for 2 hours, the amount of the byproduct is 2.1%, and in Example 10 where the reaction temperature and time are 40° C. and 2 hours, the amount of the byproduct is 3.7%).

Comparative Example 1

Example 7 of U. S. Pat. No. 5,175,345 was repeated.

That is, 13.2 g of a hydrogen fluoride (HF)/pyridine (Py) mixture (HF/Py =95/5 (wt/wt), containing about 627 mmol of the hydrogen fluoride) and 19.3 g (193 mmol) of fluorosulfuric acid were charged into a 50 ml autoclave having an internal cylinder made of Teflon, and cooled to 0° C. 3.6 Grams (30.5 mmol) of methyl 2-hydroxyisobutyrate was added, and then, the mixture was heated to 20° C. and allowed to react for 18 hours. After the reaction finished, the reaction mixture was poured into ice water and extracted with methylene chloride. A methylene chloride extract was dried over anhydrous sodium sulfate, and then methylene chloride was distilled off. The remainder was distilled to give 2.67 g (yield 73%) of methyl 2-fluoroisobutyrate having a boiling point of 70° C. (150 mmHg). The so-obtained methyl 2-fluoroisobutyrate had a boiling point under atmospheric pressure of 106° to 107° C. It was found that methyl methacrylate was formed as a byproduct in an amount of as much as 8%.

When the above Examples 1 to 16 and Comparative Example 1 are compared, it is clearly seen that, according to the process of the present invention, 2-fluoroisobutyric acid or its ester can be obtained at high yields while preventing the formation of MMA as a byproduct as compared with the process described in U. S. Pat. No. 5,175,345 which is a prior art.

Effect of the Invention

As described above, according to the present invention, there is provided a process which enables the production of 2-fluoroisobutyric acid or its ester in a simple apparatus at high yields while preventing the formation of a byproduct.

We claim:

1. A process for the production of 2-fluoroisobutyric acid or its ester, which comprises reacting 2-hydroxyisobutyric acid or its ester with thionyl chloride and a hydrogen fluoride source.

2. The process according to claim 1, wherein the 2-hydroxyisobutyric acid or its ester is reacted with the thionyl chloride, and then a reaction mixture is reacted with the hydrogen fluoride source.

3. The process according to claim 2, wherein the 2-hydroxyisobutyric acid ester is reacted with the thionyl chloride, and then the reaction mixture is reacted with the hydrogen fluoride source to obtain 2-fluoroisobutyric acid ester.

4. The process according to any one of claims 1 to 3, wherein the thionyl chloride is used in an amount of 0.5 to 5 mol per mole of the 2-hydroxyisobutyric acid or its ester.

5. The process according to claim 4, wherein the thionyl chloride is used in an amount of 0.8 to 1.5 mol per mole of the 2-hydroxyisobutyric acid or its ester.

6. The process according to any one of claims 1 to 3, wherein the hydrogen fluoride source comprises hydrogen fluoride or a mixture of hydrogen fluoride with an amine.

7. The process according to any one of claims 1 to 3, wherein the hydrogen fluoride source is used which is capable of generating hydrogen fluoride in an amount of 1 to 50 mol per mole of the 2-hydroxyisobutyric acid or its ester.

8. The process according to claim 7, wherein the hydrogen fluoride source is used which is capable of generating hydrogen fluoride in an amount of 5 to 30 mol per mole of the 2-hydroxyisobutyric acid or its ester.

9. The process according to claim 8, wherein the hydrogen fluoride source is used which is capable of generating hydrogen fluoride in an amount of 7 to 15 mol per mole of the 2-hydroxyisobutyric acid or its ester.

* * * * *